(12) United States Patent
Zhang (10) Patent No.: US 8,396,541 B2
(45) Date of Patent: Mar. 12, 2013

(54) SIGNAL ANALYSIS OF CARDIAC AND OTHER PATIENT MEDICAL SIGNALS

(75) Inventor: Hongxuan Zhang, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 913 days.

(21) Appl. No.: 12/254,245

(22) Filed: Oct. 20, 2008

(65) Prior Publication Data

US 2009/0112106 A1 Apr. 30, 2009

Related U.S. Application Data

(60) Provisional application No. 60/982,232, filed on Oct. 24, 2007.

(51) Int. Cl.
*A61B 5/046* (2006.01)
(52) U.S. Cl. .................. 600/515; 600/518
(58) Field of Classification Search .......... 600/300, 600/515–518
See application file for complete search history.

(56) References Cited

U.S. PATENT DOCUMENTS

| | | | |
|---|---|---|---|
| 4,422,459 A | 12/1983 | Simson | |
| 5,025,794 A | 6/1991 | Albert et al. | |
| 5,271,411 A | 12/1993 | Ripley et al. | |
| 5,447,519 A * | 9/1995 | Peterson | 607/5 |
| 5,464,435 A * | 11/1995 | Neumann | 607/9 |
| 5,683,429 A | 11/1997 | Mehra | |
| 5,954,664 A | 9/1999 | Seegobin | |
| 5,968,079 A | 10/1999 | Warman et al. | |
| 6,490,479 B2 | 12/2002 | Bock | |
| 6,491,629 B1 | 12/2002 | Bousseljot et al. | |
| 6,501,983 B1 | 12/2002 | Natarajan et al. | |
| 6,572,560 B1 | 6/2003 | Watrous et al. | |
| 6,597,943 B2 | 7/2003 | Taha et al. | |
| 6,768,969 B1 * | 7/2004 | Nikitin et al. | 702/188 |
| 6,904,390 B2 | 6/2005 | Nikitin et al. | |
| 7,177,682 B2 | 2/2007 | Lovett | |
| 7,277,745 B2 | 10/2007 | Natarajan et al. | |

FOREIGN PATENT DOCUMENTS

WO WO 2004/098707 11/2004

OTHER PUBLICATIONS

Shimizu S, Osaka M, Saitoh H, Atarashi H, Takano T, "Quantitative analysis of termination of vagally induced canine atrial fibrillation by mutual information", Jpn Circ J. Feb. 2001, vol. 65, No. 2, p. 111-116.

Paul, J.S.; Luft, A.R.; Hanley, D.F.; Thakor, N.V., "Coherence-weighted wiener filtering of somatosensory evoked potentials", IEEE Transactions on Biomedical Engineering, vol. 48, Issue 12, Dec. 2001 p. 1483-1488.

* cited by examiner

*Primary Examiner* — Rex R Holmes
(74) *Attorney, Agent, or Firm* — Alexander J Burke (57) ABSTRACT

A system and method provide detecting and monitoring cardiac electrophysiological changes by determining differences between a reference signal representing a heartbeat signal and an analysis signal representing another heartbeat signal. A set of signal data consisting of a number of heartbeat signals is acquired as a function of time. Individual heartbeat signals within the set of acquired signals are identified, an individual signal comprising data values representing a plurality of sample points during a single heartbeat. One of the identified individual signals or a derived signal representing an average of a subset of the identified individual signals is selected as an analysis signal. A reference signal is identified. The sample points of the reference signal are aligned with the sample points of the analysis signal. A single value representative of mutual correspondence between the sample points of the reference signal and the corresponding sample points of the analysis signal is calculated. Data indicating a calculated value is communicated to a destination for viewing by a user.

17 Claims, 5 Drawing Sheets

SIGNAL ANALYSIS OF CARDIAC AND OTHER PATIENT MEDICAL SIGNALS

This is a non-provisional application of provisional application Ser. No. 60/982,232 filed Oct. 24, 2007, by H. Zhang et al.

FIELD OF THE INVENTION

This invention concerns a system and method for analyzing cardiac electrophysiological signals, for example through comparison and analysis of selected signals and through arrhythmia pattern analysis for use in making decisions affecting cardiac medical treatment.

BACKGROUND OF THE INVENTION

Early detection and characterization of cardiac arrhythmias, such as myocardial ischemia and infarction, are critical for management of cardiac disorders and irregularities. Because cardiac arrhythmias can usually be indicated and monitored by cardiac electrophysiological changes, cardiac signals, both surface ECG signals and intra-cardiac electrograms, are monitored for diagnosis. Signal features corresponding to certain aspects of each heartbeat are extracted and analyzed to assist in the identification of various cardiac pathologies.

The surface electrocardiogram (ECG or, sometimes, EKG), obtained by recording the potential difference between two electrodes placed on the surface of the skin, produces a time-varying electrical signal indicative of changes in electrical potential during a heartbeat. A single normal cycle of the ECG represents the successive atrial and ventricular depolarization and repolarization that occur with each heartbeat as the cardiac muscle fibers alternately contract and relax. The electrical changes result in peaks and troughs of the ECG waveform, conventionally labeled P, Q, R, S and T, and recorded as deviations from the base or isoelectric level of the signal. Atrial depolarization produces the P-wave. Because the ventricles are larger in mass than the atria, the subsequent atrial repolarization is largely obscured by the QRS complex that represents the concurrent ventricular depolarization. The ST segment, culminating in the T-wave, represents ventricular repolarization.

Currently, waveform morphologies and corresponding medical parameter analysis of cardiac depolarization and repolarization processes for various portions of the ECG signal, including waveform shape and electrophysiological action potential changes of the P-wave, QRS complex, ST segment, and T-wave, are widely utilized for cardiac arrhythmia monitoring and identification. However, analysis of electrophysiological signals is often a subjective and time-intensive procedure, requiring expertise and clinical experience for proper interpretation.

In addition, there are several problems with current biomedical signal processing strategies for detection and monitoring of cardiac arrhythmias. Accurate analysis of electrophysiological signals is complicated by electrical noise, patient movement, and other bio-noise (respiration, etc), which can significantly affect and distort the small voltage cardiac electrophysiological signals, possibly resulting in unreliable diagnosis and improper characterization of various arrhythmias. Potential problems can occur, for example, in the detection and assessment of acute myocardial ischemia during a Percutaneous Transluminal Coronary Angioplasty (PTCA) procedure, often resulting in ST segment distortion. Ischemia occurs when the oxygen supplied by the coronary arteries is insufficient to meet the demands of the myocardium. This condition often appears during the PTCA procedure, as the artery is temporarily occluded. Similar diagnostic problems can occur in the detection of atrial fibrillation during an electrophysiologic (EP) procedure in the operating room, commonly resulting in P-wave distortion; and in long term signal diagnosis during Holster cardiac monitoring, which calls for analysis of cardiac signal morphology distortion; as well as in other arrhythmias.

Typically, the standards and criteria clinicians utilize for diagnosing cardiac pathology and malfunction focus on the main electrophysiological changes of the signal. However, because the pathology-related changes are distributed throughout both the depolarization and repolarization processes, current diagnosis and pathology evaluation methods, such as ST segment deviation as a criterion for monitoring ischemia cases, do not utilize all the information available in a signal. Ischemia is commonly diagnosed using ST segment analysis. The ST segment, lying between the end of the QRS complex and the initial deflection of the T-wave, is normally isoelectric. It corresponds to the first phase of ventricular repolarization following the QRS complex. Elevation or depression of the ST segment is considered clinically important as an indication of ischemia. In typical instances of ischemia, the ECG signal may not return to its baseline or isoelectric level (represented in the interval between the P-wave and the QRS complex) until after the T-wave. The level of the ST segment relative to the isoelectric level, termed the ST deviation, is conventionally measured at a single point 80 milliseconds after the end of the QRS complex. An ST deviation of 100 microvolts ($\mu V$) in surface ECG signals is a common standard for clinical significance and diagnosis of ischemia. However, ST segment changes, as well as QRS complex changes, are not necessarily obvious and are not easily qualitatively and quantitatively captured and characterized by such traditional methods as action potential displacements.

ST segment analysis presents significant deviation and error rates in ischemia/infarction characterization. Pathological changes, particularly during the ventricular depolarization within the QRS complex, may not be extracted and accurately captured by simple ST deviation measurement. Also, bio-noise may distort the ST segment, which is a low-frequency, shifting signal. There are currently no accepted criteria or methods for assessing the severity of ischemia via interpretation of the action potential voltage. Moreover, current clinical methods and strategies do not provide adaptive calculations and monitoring. The lack of adaptive monitoring may delay diagnosis, resulting in late medical decisions and delayed cardiac rhythm management. Furthermore, there are no standards or criteria for ST segment analysis to detect and characterize ischemia utilizing intra-cardiac electrograms. There is a need for a more sensitive, versatile and reliable signal analysis and characterization to capture minute pathological changes in cardiac action potentials.

Some recent research has begun to apply more sophisticated mathematical theories to biomedical signal interpretation, such as frequency analysis (e.g., FFT analysis, dominant frequency analysis, etc.), signal modeling analysis, and non-linear entropy evaluation, but most research strategies focus on generating a new pathology index for qualitative characterization of cardiac arrhythmia.

Therefore, a need exists to apply different signal analysis algorithms to develop a more accurate and predictive measure of cardiac electrophysiological signals. A system and method according to invention principles addresses these deficiencies and related problems.

SUMMARY OF THE INVENTION

A system and method provide detecting and monitoring cardiac electrophysiological changes by determining differences between a reference signal representing a heartbeat signal and an analysis signal representing a different heartbeat signal. A set of signal data representing a plurality of cardiac electrophysiological signals is acquired as a function of time. Individual heartbeat signals within the set of acquired signals are identified. An individual signal includes data values representing a plurality of sample points during a single heartbeat. One of the identified individual signals or a derived signal representing an average of a subset of the identified individual signals is selected as an analysis signal. A reference signal comprising data values representing a plurality of sample points is identified. The sample points of the reference signal are aligned with the sample points of the analysis signal. A single value representative of the mutual correspondence of the signals is calculated between the sample points of the reference signal and the corresponding sample points of the analysis signal. A user is notified of the calculated value.

DETAILED DESCRIPTION OF THE INVENTION

A system performs signal analysis on, for example, cardiac electrophysiological signals. Cardiac signals, both surface ECG signals and intra-cardiac electrograms, are a combined signal of a multi-cardiac-cell electrophysiological response to stimulation, either from the sinoatrial node or from another stimulator. These signals reflect cell electrical activities which exhibit a harmonic rhythm in a group manner. Hence, information theory provides an appropriate basis for cardiac signal analysis and characterization. For example, if some cells in the atrium or ventricle are injured, cardiac electrophysiological responses and electrical excitations from these cells may be delayed or attenuated. This may cause partial distortion of and morphology changes to the cardiac signals, such as P-wave distortion or duplication in atrial fibrillation and atrial flutter, or ST segment deviation in ischemia and infarction.

A system performs cardiac signal processing and mutual correspondence analysis using information in a cardiac signal, including both amplitude and latency (phase). A cardiac electrophysiological signal represents a combined group signal of a number of myocardial cells, and system analysis using mutual correspondence improves diagnostic accuracy and precision. The mutual correspondence of two signals, also referred to as mutual synchronicity, is a single value that represents the similarity or mutual information of two signals by comparing the values of at least one respective signal parameter over a range of corresponding sample points. The mutual correspondence effectively and efficiently characterizes the difference between the two signals by comparing corresponding sample points. Mutual correspondence based cardiac signal analysis utilizes both heart depolarization (P-wave and QRS complex data) and repolarization (ST segment data) signals for arrhythmia capture, providing enhanced sensitivity and higher reliability. The mutual correspondence based cardiac signal analysis utilizes more of the heart electrophysiological signals and data for arrhythmia analysis and advantageously reduces the effects of remaining noise and artifacts, providing more stable signal characterization. The system automatically provides the results of analysis of cardiac electrophysiological signal data, decreasing the requirements for medical expertise and clinical experience and enabling more accurate interpretation of the signal data.

Mutual correspondence based cardiac pathology and malfunction diagnosis and characterization provides a more precise approach to identifying cardiac disorders, predicting cardiac pathology occurrence, and diagnosing cardiac malfunction characteristics. This advantageously provides a measure value that enables a user to more precisely and reliably make medical decisions and suggest clinical treatment options, such as drug delivery and long term cardiac care. The present arrangement provides several advantages over the current clinical approaches and research methods. Mutual correspondence is utilized adaptively as a multi-dimensional calculation, such as time and frequency analysis, and characterizes both temporal and spatial information of cardiac signals. The system enables a user to track the cardiac patient over a long term and is useful in detecting a secondary cardiac event by contrasting inter-trial variability with injury/recovery related physiological changes.

Embodiments of the present system concern an arrhythmia analysis process involving cardiac signal pattern recognition based on the mutual correspondence of the signal data. Additionally, the system employs cardiac signal discrimination and characterization based on intrinsic mode analysis. Mutual correspondence based cardiac signal pattern recognition and analysis is implemented utilizing myocardial ischemia and infarction as examples of cardiac arrhythmia. However, a mutual correspondence cardiac signal pattern recognition method is also applicable to other cardiac arrhythmia analysis and diagnosis. The system utilizes a calculation of mutual correspondence between a heartbeat signal selected for analysis and a reference signal, for the detection and the qualitative and quantitative characterization of cardiac electrophysiological changes.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

The mutual correspondence of two signals, as used herein, comprises a calculated value representative of any of a similarity, difference or mutual information of corresponding sample points of the two signals over a set of sample points. The inventors have recognized that the application of information theory based cardiac signal processing together with mutual correspondence analysis of cardiac electrophysiological signals, produces an enhanced measurement value that is useful in analysis and diagnosis of patient conditions. Information theory analysis well known in the art includes probability, entropy, and mutual information analysis and associated calculations and associated parameters which are employed in the application of mutual correspondence analysis.

A respective cardiac electrophysiological signal is a random variable, with the sampled values of the signal as events representing the outcomes of independent trials. It is thus possible to determine a probability distribution for the signal values by summing, for each signal value (or range of signal values) in the sample set, the number of points equal to that value, and dividing each sum by the total number of sampled values. The joint probability distribution of two signals S1 and S2 is the probability that both $s1_i=a$ and $s2_i=b$ for values a, b at each point i over all sample points $0<i<N+1$. If $s1_i=a$ and $s2_i=b$ are independent events, their joint probability distribution is equal to the product of the probability of S1 and S2. In general, the joint probability is $$p(S1, S2) = p(S1) \cdot p(S2|S1)$$

or the product of the probability of $s1_i=a$ and the probability of $s2_i=b$, given that $s1_i=a$ has occurred.

Entropy, or the information energy within a signal, is a measure of the uncertainty associated with a random variable. The entropy of a signal quantifies, in the sense of an expected value, the information contained in the signal, usually in units such as bits. The entropy of two probability distributions $P_X$ and $P_Y$ is represented as $$H(XY) = -\sum_{(x,y)} p_{xy} \log(p_{xy})$$

Mutual information is the shared information between two signals. It is the amount of information gained about X when Y is known, and vice versa. Mutual information is represented as $I(X,Y)=H(P_X)+H(P_Y)-H(P_{XY})$. When two signals contain zero mutual information, the signals represent independent random variables. Two identical signals have mutual information equal to 1. However, a signal and its mirror image also have mutual information equal to 1. Thus, a different measure to quantify signal similarity or difference can provide a better diagnostic quantity.

Figure 1:
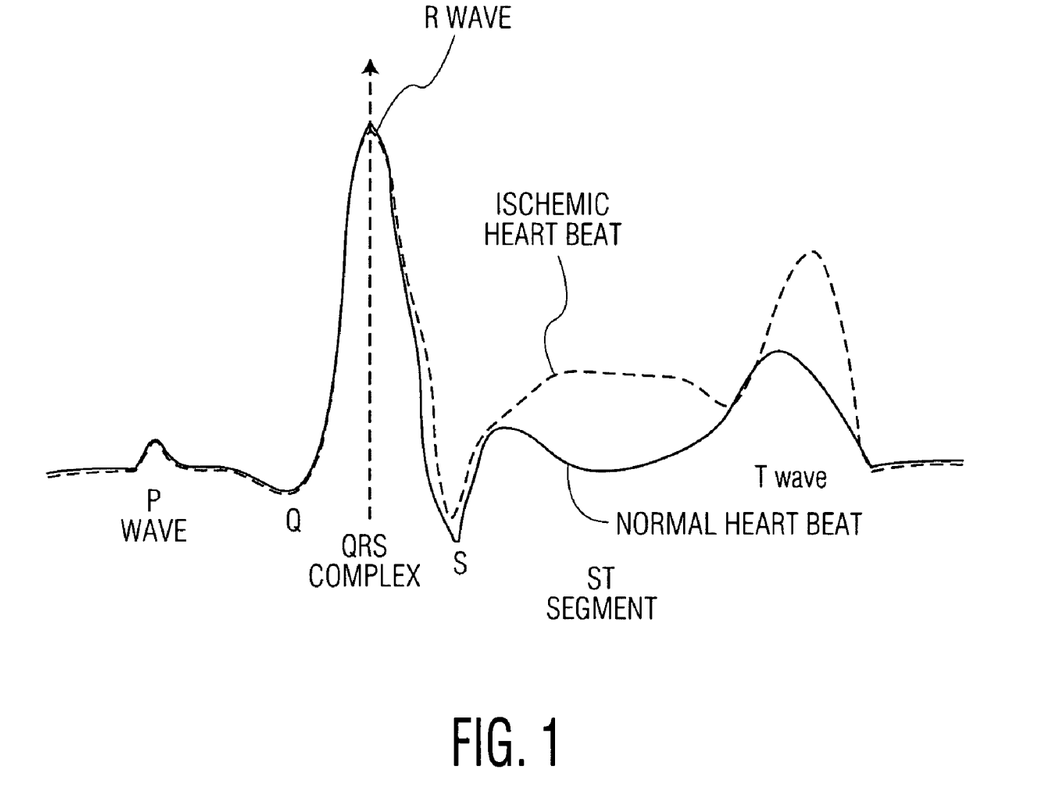
FIG. 1 illustrates a comparison of single heartbeat signals for a healthy heartbeat and an ischemic heartbeat.
Figure 2:
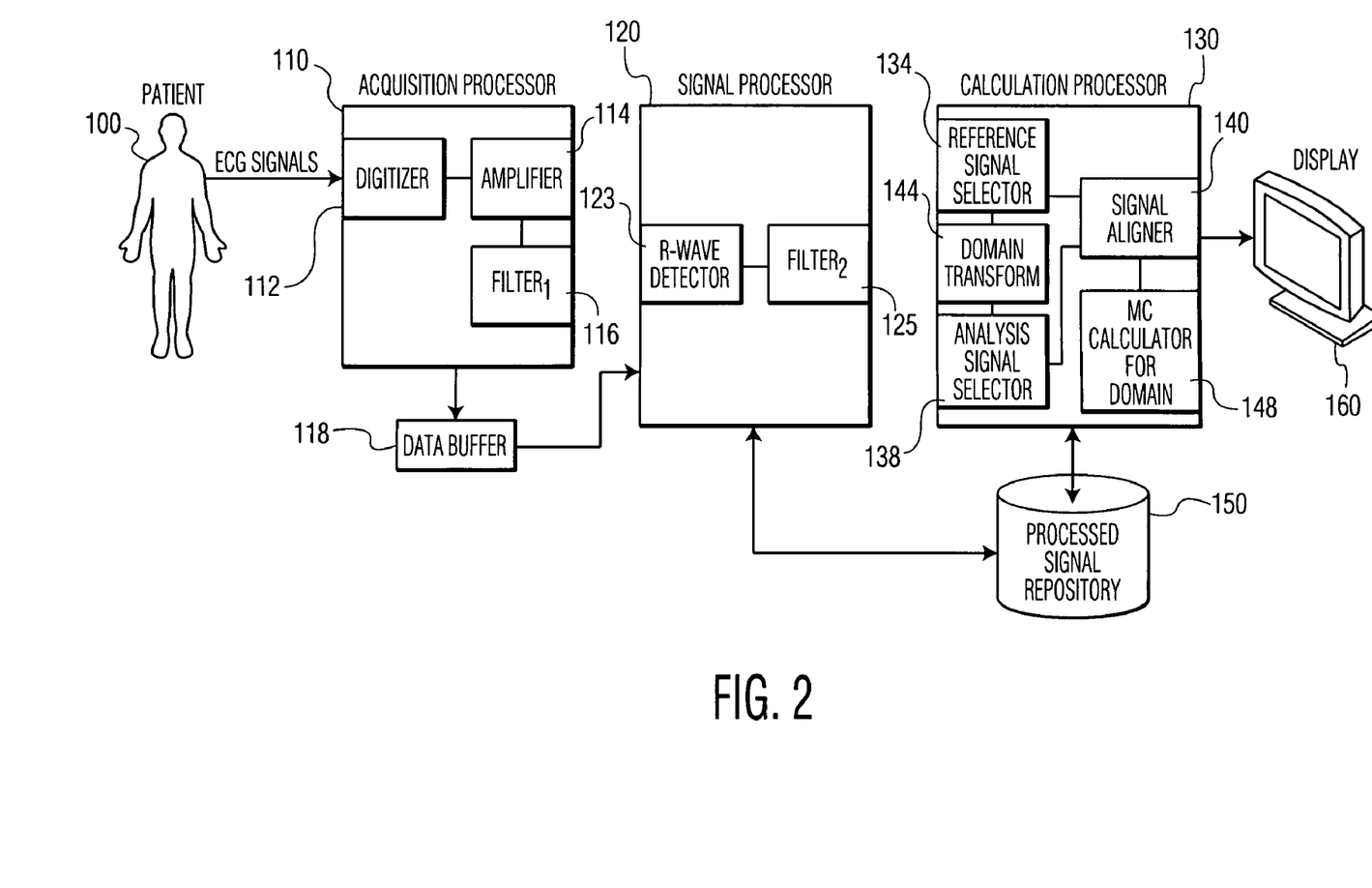
FIG. 2 shows a functional block diagram of a system for analysis of cardiac arrhythmias utilizing mutual correspondence of electrocardiogram signals to detect and characterize cardiac arrhythmias according to invention principles.

FIG. 1 illustrates the comparison of single heartbeat signals for waveforms representing a healthy heartbeat and an ischemic heartbeat. As shown herein, the healthy heartbeat signal is represented by a solid line waveform and the ischemic heartbeat signal is represented by the dashed line waveform. This is a time domain (one dimensional) signal comparison and analysis, in which electrical potential differences between leads, or signal voltages, are represented as a function of time. The normal adult heart undergoes such a depolarization-repolarization cycle 60 to 90 times per minute, or approximately once per 850 milliseconds (ms). From a reference or isoelectric potential level, atrial depolarization is shown by the upward deflection labeled as the P-wave. The signal then returns to the isoelectric level, before a small downward deflection, labeled Q, that marks the beginning of the QRS complex. The maximum upward deflection of the signal is labeled R. The maximum downward deflection is labeled S. The QRS complex reflects ventricular depolarization. Its normal duration in adults is 100-116 ms. in adults, with times generally shorter in females than in males. The maximum value of the R deflection is generally about 0.7 millivolts (mV). The small upward deflection following the QRS complex is labeled the T-wave, and represents ventricular repolarization. The QT interval, from the beginning of the Q deflection to the end of the T deflection, is normally about 400 ms in duration. A small U wave following the T-wave, visible in some, but not all, ECGs, is not shown in this image FIG. 2 illustrates the components of a system for analysis of cardiac arrhythmias utilizing mutual correspondence of electrocardiogram signals to detect and characterize arrhythmias. One skilled in the art should recognize that any of the component elements shown in FIG. 2 (and elsewhere) may be embodied as electronic circuitry, hardware, software or any combination thereof and, while described as separate components, the system may be modified to include multifunctional circuits, hardware, software and any combination thereof. An acquisition processor 110 acquires electrocardiogram signals (ECG) using conventional processes. Signals are received through electrodes attached to patient 100 in a known manner. In a digitizer 112, the analog signals are sampled and quantized and digitized. The amplifier 114 amplifies the signal data to levels appropriate for further processing, and a first filter 116 filters signals to remove some noise and artifacts, through means known in the art. Filtered and amplified signals are placed in a data buffer 118 for additional processing.

A signal processor 120 is connected to the data buffer 118 and receives the filtered amplified signals. The signal processor 120 performs further processing of the signals. An R-wave detector 123 identifies local maximum amplitudes in order to recognize and separate an electrocardiogram signal representative of a single heartbeat signal from the set of electrocardiogram signals in the data buffer 118. One skilled in the art will recognize that, while the system provides the above mechanism for identifying individual signals, other mechanisms for performing individual signal identification from the data set may be used are known and may be incorporated for use by the system. A second filter 125 performs additional processing to further remove noise and artifacts in this processor. Various ECG artifact removal methods, including high pass filtering, spike clipping, template subtracting, wavelet thresholding, and adaptive filtering, may be performed. Processed signals are saved in a repository 150 as the current signal set for subsequent analysis.

The calculation processor 130 is connected to the repository 150 and retrieves the signals for performing a mutual correspondence analysis. A reference signal selector 134 identifies a single signal as the reference signal for later comparison and analysis. The reference signal is selected from the acquired current signal set of acquired identified individual signals in the repository 150. For example, selecting an initial signal from the patient as the reference signal is appropriate for a patient undergoing an electrophysiological (EP) procedure. Another exemplary method of selecting the reference signal is selecting a signal acquired from a database of previous signals from this patient for adaptive monitoring of a particular patient. Alternatively, the reference signal is selected by a matching process resulting from a query of a database of signals from other patients identified by gender, age, weight, physical condition, and other individual characteristics, or from a database containing reference signals derived through an averaging calculation.

An analysis signal selector 138 retrieves a signal from the acquired current signal set for analysis. A signal aligner 140 automatically aligns the analysis signal with the reference signal by, for example, matching the R-waves of the analysis signal and the reference signal and adjusting the signal data sets to put sample points of the two signals in correspondence with each other. An MC calculator 148 computes a value representing the mutual correspondence of the two signals according to equations appropriate for the domain and clinical environment. The sum of the differences between the data value of each sample point in the analysis signal and each corresponding sample point in the reference signal is calculated and normalized by dividing by the number of sample points. The mutual correspondence value computed is sent to the display 160 and stored in the repository for future reference.

In additional embodiments of the system, the calculation processor includes one or more domain transforms 144. The domain transform 144 converts the acquired signal data from a data set in the time domain (signal amplitude vs. time) to a data set in another different domain, such as the frequency domain (magnitude and phase of signals vs. frequencies).

The value representing the mutual correspondence calculated by calculation processor 130 encapsulates information indicating pathology and cardiac malfunction related changes and more sensitively characterizes signal distortion and changes. Information theory analysis is employed using a signal parameter, e.g., amplitude. Given two processes, the corresponding output signals may be designated $S_1$ and $S_2$. One dimensional mutual correspondence of $S_1$ and $S_2$ may be represented by $$MC(S_1, S_2) = \sum_{i=1}^{N} p_i(s_{1i}, s_{2i})/N$$

where $p_i$ is the joint probability of signal values $s_{1i}$ and $s_{2i}$ at sample point i, and the probability is summed over all N sample points, then normalized by dividing the sum by the value N.

Figure 3:
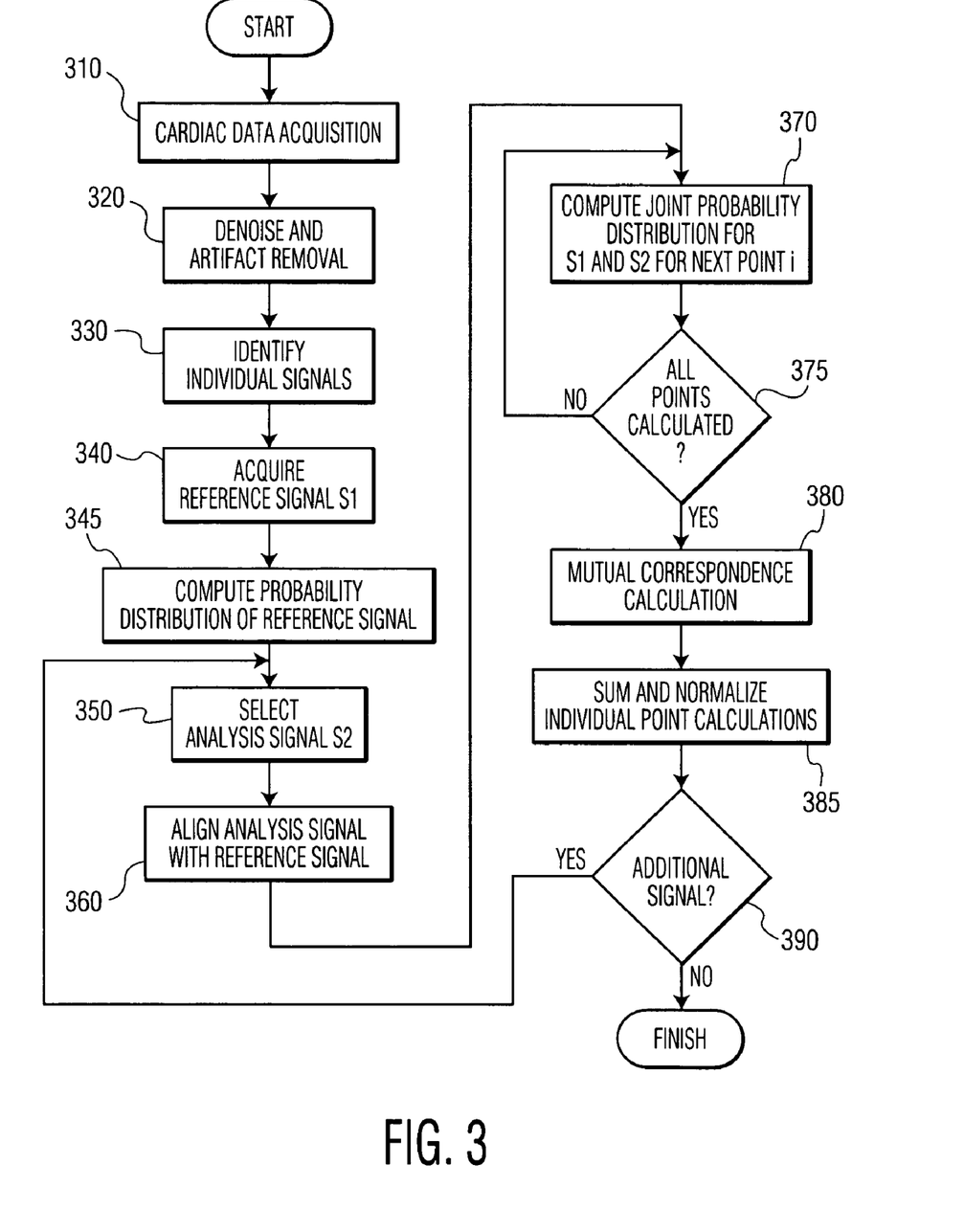
FIG. 3 shows a procedure for a unified one-dimensional mutual correspondence analysis and calculation according to invention principles.

FIG. 3 illustrates a flow chart for a method of calculating the mutual correspondence of two signals, $S_1$ and $S_2$ automatically performed by the system of FIG. 2. A set of electrocardiogram signals is acquired in step 310. Preprocessing removes noise and artifacts by known methods in step 320. Individual signals within the acquired set of electrocardiogram signals are identified and separated in step 330. This is accomplished by known methods such as R-wave identification, for example. A reference signal $S_1$ is acquired in step 340, and the probability distribution of its amplitude values is determined over the set of sample points by known methods in step 345. An individual signal $S_2$ is selected from the set for analysis in step 350. Corresponding time sequences of $S_1$ and $S_2$ with the same number of sample points are identified in step 360 by aligning the reference and analysis signals. The joint probability of $S_{1i}$ and $S_{2i}$ is computed for each point i in the sample space in steps 370 and 375. The point by point mutual correspondence of $S_1$ and $S_2$ is then calculated in step 380, and the value of $MC(S_1, S_2)$ is calculated by summing and normalizing over the sample space in step 385. If there are additional analysis signals in the set, the calculation of mutual correspondence is repeated according to step 390.

In an alternative embodiment, calculation of mutual correspondence is performed using $$MC(S_1, S_2) = \left[\sum_{i=1}^{N} \min\_amplitude(s_{1i}, s_{2i})\max\_amplitude(s_{1i}, s_{2i})\right]/N$$

wherein $S_1$ is the reference signal represented over a set of sample points i numbered from 1 to N, $S_2$ is the analysis signal represented over a set of sample points i numbered from 1 to N, $\min\_amplitude(s_{1i}, s_{2i})$ is the lesser of the data values of $s_{1i}$ and $s_{2i}$ for each corresponding sample point i, and $\max\_amplitude(s_{1i}, s_{2i})$ is the greater of the data values of $s_{1i}$ and $s_{2i}$ for each corresponding sample point i. In this calculation, the difference in amplitude between corresponding sample points of the signal is used to obtain the measure of signal similarity. Again, however, the mutual correspondence value compares corresponding data points over the entire heartbeat signal, capturing any kind of morphology changes in the signal as compared with the reference signal.

Mutual correspondence calculation based on the analysis of a single heartbeat signal extracts arrhythmia information for a particular patient. However, because a single heartbeat signal may be easily distorted by many types of noise, heartbeat averaging is sometimes utilized to improve the signal quality before further analysis is performed. The additional procedure of signal averaging may be added to the Signal Processor 120 shown in FIG. 2. After R-wave detection is used for individual signal identification, cardiac signal averaging is applied for additional noise and artifact rejection, e.g., averaging over 5-10 heartbeat signals. This averaging algorithm is utilized adaptively based on detected noise and artifacts levels in the signals. The averaged signal is then used as the analysis signal for mutual correspondence calculation with cardiac heartbeat synchronization, according to the earlier developed function:

$$MC(\overline{S_1}, \overline{S_2}) = \sum_{i=1}^{N} p_i(\overline{s_{1i}}, \overline{s_{2i}})$$

in which $MC(\overline{S_1}, \overline{S_2})$ is the mutual correspondence based on probability calculation, $P_i(\overline{s}_{1,i}, \overline{s}_{2,i})$ is the joint probability between corresponding points of averaged signals $\overline{S}_1$ and $\overline{S}_2$, and N is the number of sample points in $\overline{S}_1$ and $\overline{S}_2$. The mutual correspondence value calculated is used for ischemia and infarction estimation, diagnosis, and prediction. In the present arrangement, the mutual correspondence calculation utilizes an averaged heartbeat signal for calculation.

As the comparison of the normal heartbeat and ischemic heartbeat signals in FIG. 1 shows, there are significant differences between the signals, especially from the peak of the R-wave through the end of the T-wave. These differences are more completely captured in the calculation of mutual correspondence than by use of the single reference point at 80 ms. following the QRS complex. Based on QRS complex/R-wave detection, the two kinds of heartbeats (the healthy heartbeat signal is used as a reference signal) is aligned, and the mutual correspondence calculated as described above.

Figure 4:
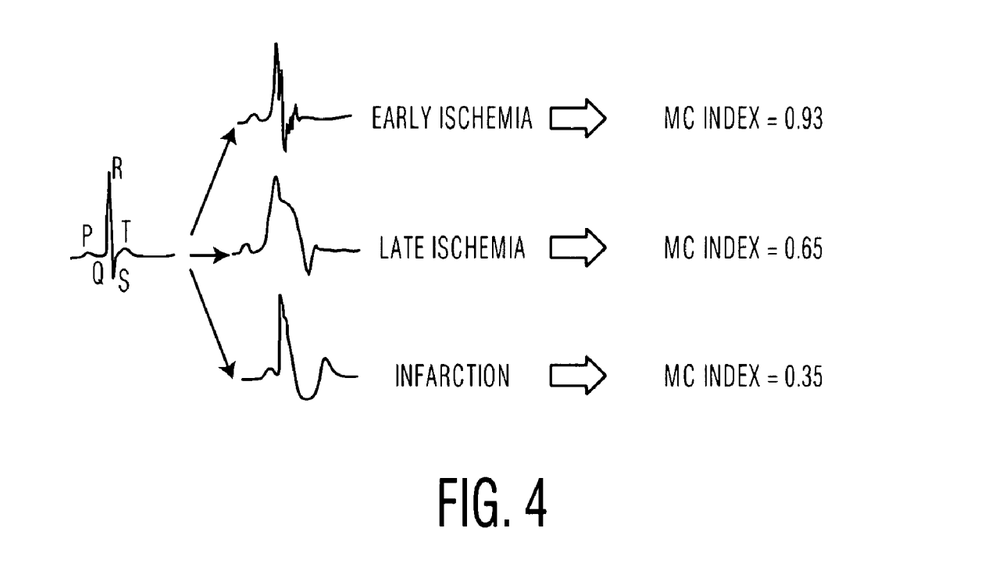
FIG. 4 shows data resulting from a unified one dimensional mutual correspondence analysis during an exemplary angioplasty procedure according to invention principles.

FIG. 4 illustrates a one-dimensional mutual correspondence calculated according to invention principles for different stages of ischemia. This example illustrates cardiac signals and mutual correspondence calculations during an animal PTCA (Percutaneous Transluminal Coronary Angioplasty) experiment. The mutual correspondence value is 0.98 (not shown) when calculated comparing reference normal healthy heart signals. During a short term occlusion, balloon inflation, which nearly results in an infarction, the value decreases to 0.35. After the reperfusion procedure, the value goes back to normal, MC=0.95. In the figure, the mutual correspondence calculations for signals at three different stages of the procedure, early ischemia (MC=0.93), late ischemia (MC=0.65), and infarction (MC=0.35), are shown. As the data illustrates, mutual correspondence calculation and analysis separates and discriminates the severity of the ischemia and infarction. In the preferred embodiment, mutual correspondence calculation and analysis is utilized not only for signal comparison, but also for continuous clinical real-time monitoring and diagnosis, and for pathology trend prediction.

Alternatively, mutual correspondence is calculated for multi-channel signals (for example, cardiac signals from different leads of an electrocardiogram). The separate calculations of mutual correspondence using signals from different leads are advantageously combined by averaging to produce a single mutual correspondence value for use by a healthcare professional in diagnosis and monitoring of patient pathologies. The mutual correspondence value produced by the system may also be used in monitoring and diagnosing pathologies and malfunctions of the heart and cardiac circulation system during other cardiac arrhythmias, such as atrial fibrillation and ventricle tachycardia. With adaptive analysis, a cardiac patient is monitored during long term analysis. This method is especially useful for detecting a secondary cardiac event by differentiating inter-trial signal variability from the injury/recovery related physiological changes.

Figure 5:
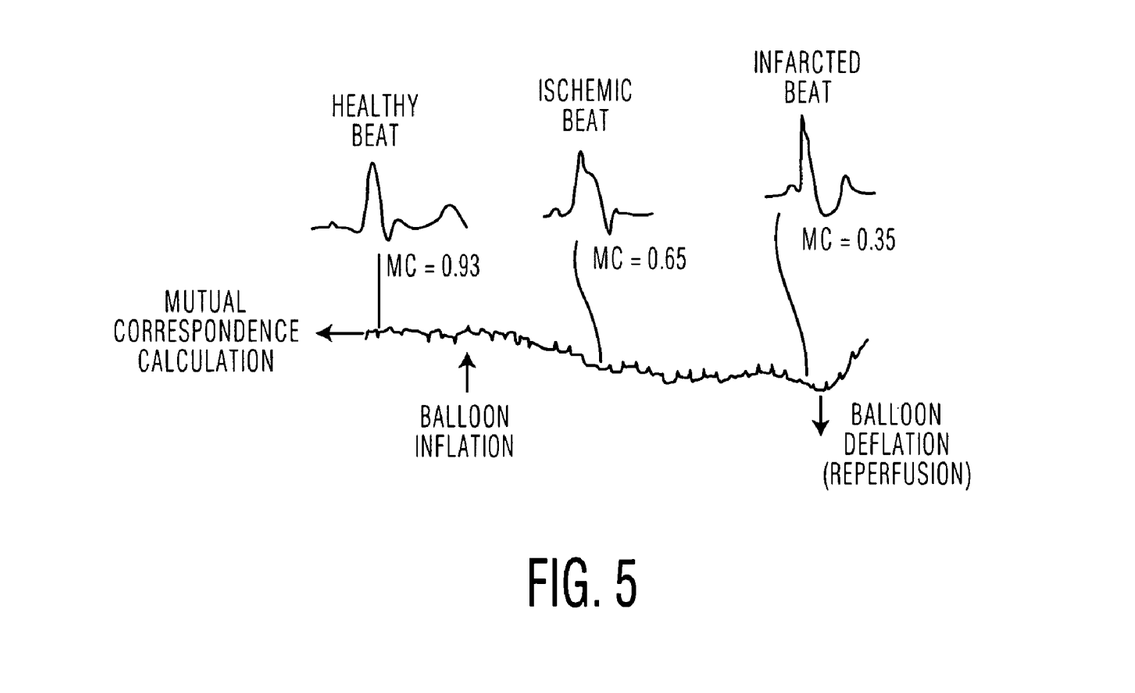
FIG. 5 shows the three different intrinsic modes exhibited during continuous real-time signal pattern/mode analysis for myocardial ischemia detection and characterization according to invention principles.

Cardiac electrophysiological response is utilized as an intrinsic signature for heart function. Data representative of a heartbeat signal may be used as an intrinsic mode for pattern recognition and characterization of cardiac pathology and heart malfunction. For example, during a PTCA procedure, balloon inflation may cause low blood flow in the specific area in the myocardium to result in breaking the cardiac cell activity harmonic frequencies. The electrophysiological response and working mode switches from healthy to ischemic. The rhythm and mode transition is extracted and characterized by the cardiac signals. Mutual correspondence, employing information theory, captures these changes and the transition of the cardiac intrinsic mode. During ischemia, for example, the energy in the mid-frequency band, around 20 to 40 Hz, exhibits significant changes, transitioning to a characteristically different signal. FIG. 5 shows a continuous real-time signal pattern/mode analysis for myocardial ischemia detection and characterization in a PTCA procedure. In the figure, there are three obvious cardiac signal patterns (intrinsic modes) shifting to indicate three different heart and cardiac electrophysiology states: healthy heartbeat (reference signal), early ischemia and late ischemia (a possible infarcted heartbeat). The different cardiac electrophysiology patterns, intrinsic modes, are utilized as a signature of cardiac arrhythmia.

One dimensional mutual correspondence is the application of basic analysis to characterize the difference between signals and thereby discriminate cardiac electrophysiological changes. It is based on one dimensional signal information, such as time domain signals or frequency domain signals. As described above, time domain signals are utilized to calculate the mutual correspondence based on amplitude and signal latency. However, one dimensional mutual correspondence analysis is not limited to such calculations and applications. Mutual correspondence calculations may also be performed using other parameters based on mutual or bilateral information calculation and analysis, such as spectral parameters, energy distribution, or signal coherence.

Multi-dimensional mutual correspondence theory is another application of mutual correspondence analysis. Multi-dimensional mutual correspondence combines multiple parameters and signal properties for more sensitive and reliable capture and characterization of the pathology related electrophysiological changes. As shown in FIG. 2, for multi-domain mutual correspondence calculation, the signal data is transformed 144 from time domain data to, for example, frequency domain data, by a means such as the Fast Fourier Transform, to convert a sequence of signal voltage values to coefficients for a set of sinusoidal signals of differing frequencies. A mutual correspondence calculation is then performed on the transformed data, and the values calculated in the different domains are combined to produce a single result.

The multi-dimensional mutual correspondence calculation includes mutual correspondence based on time domain parameters (such as amplitude, latency, energy, etc), and frequency domain parameters (frequency distribution, spectral content, etc), as well as other domain indices, including any linear or nonlinear calculations such as various complexity measures including symbolic index complexity, and quantum density measures.

Given two signals, $S_1$ and $S_2$, one dimensional mutual correspondence is calculated based on the definition presented above. Then, $$A = MC_{time\text{-}domain} = \sum_{i=1}^{N} p_i(s_{1i}, s_{2i})$$

$$B = MC_{frequency\text{-}domain} = \sum_{i=1}^{N} q_i(s_{1i}, s_{2i})$$

in which A and B are the mutual correspondence calculations in the time domain and the frequency domain respectively, of the two signals; $p_i$ and $q_i$ are the joint probabilities between the corresponding points of signals $S_1$ and $S_2$ in the respective domains; and N is the number of sample points of $S_1$ and $S_2$. The two-dimensional mutual correspondence for time and frequency can then be represented as:

$$MC_{time\text{-}frequency} = 1 - \frac{\|A - B\|}{\|A + B\|}$$

in which $\|A\|$ is the absolute value operator applied to A.

Figure 6:
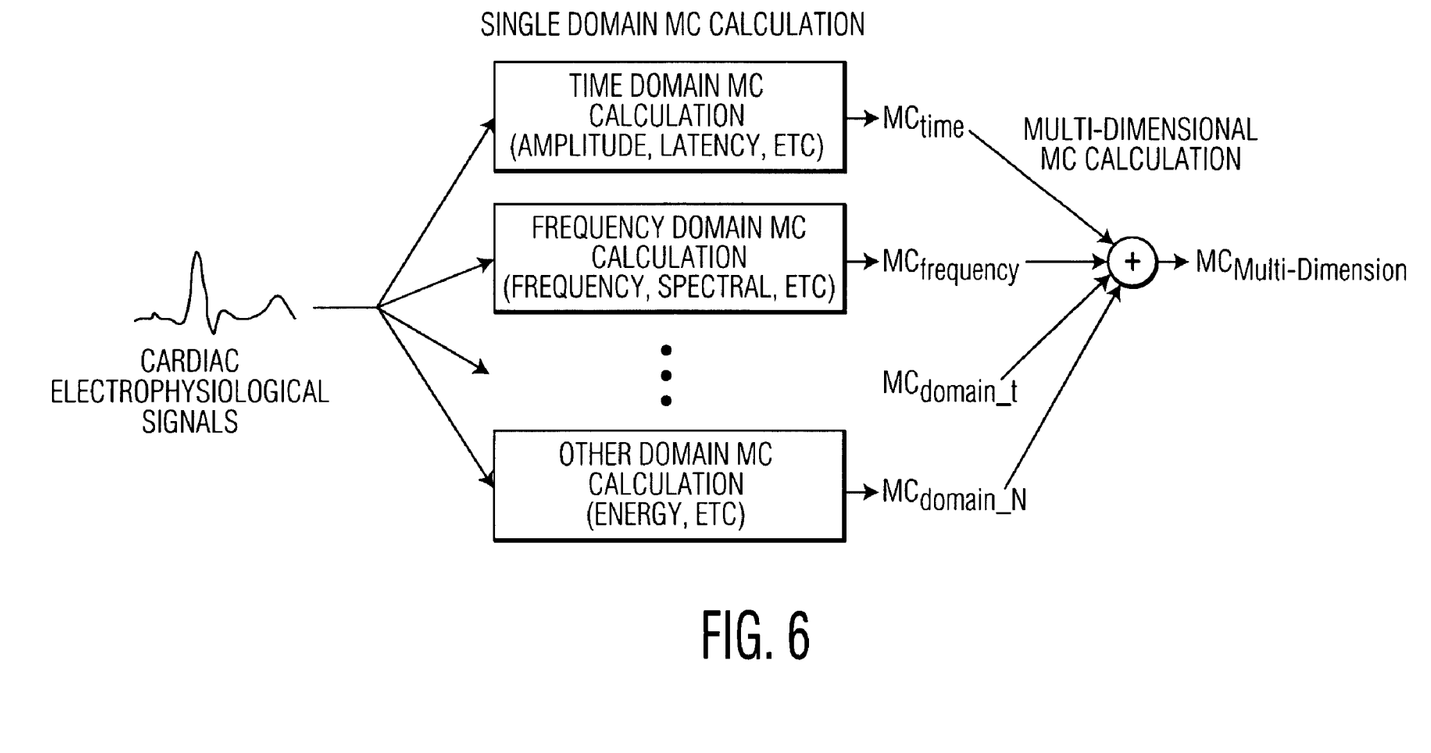
FIG. 6 is a functional block diagram detailing multi-dimensional mutual correspondence analysis and calculation according to invention principles.

If two cardiac signals, $S_1$ and $S_2$, are identical or similar, the corresponding time domain and frequency domain mutual correspondences, A and B, are similar; and the two-dimensional mutual correspondence $MC_{time\text{-}frequency}$ is nearly equal to 1. On the other hand, if the two cardiac signals differ, as they will when a healthy heart signal is compared with an ischemic signal, the cardiac signal distortion and morphology changes are mapped in the calculation of multi-dimensional mutual correspondence. When the pathological displacements and distortions in the time domain signal are difficult to track and capture by human observation, or require extensive clinical expertise, multi-dimensional mutual correspondence provides a more sensitive and reliable method for clinical application with precise diagnosis and early cardiac treatment because it is able to characterize the heart malfunction and pathology related distortion in both the time domain and the frequency domain. FIG. 6 is a diagram illustrating a working sequence for multi-dimensional mutual correspondence analysis as generalized beyond the basic time domain and frequency domain calculations.

Multi-dimensional mutual correspondence $MC_{multi\text{-}dimension}$ is represented in the general case as:

$$MC_{multi\text{-}dimension} = 1 - \frac{\sum_{N} \|A_i - \overline{A}\|}{\sum_{N} \|A_i\|}$$

in which $A_i$ is the one dimensional mutual correspondence calculation index for domain i; $\overline{A}$ is the average of the synchronicities of all domains calculated; and N is the number of domains utilized in the calculation.

The present method and system produces a value representing the mutual correspondence between two signals which is useful in monitoring and diagnosing a plurality of cardiac pathologies and malfunctions. For example, the mutual correspondence value enables a healthcare provider to more precisely and reliably diagnose cardiac arrhythmias, such as atrial fibrillation and ventricular tachycardia, which ultimately leads to improved patient care by allowing for the implementation of preventative (or time-critical) actions. Also, as described above, the mutual correspondence analysis method and strategy is selectively modifiable according to the application and signal usage. For example, in Atrial Fibrillation (AF) or atrial flutter cases, the mutual correspondence calculation is used to capture the P-wave changes, such as amplitude potential change and P-wave delay (electrophysiological activity latency). The mutual-correspondence-analysis-based P-wave distortion analysis provides a better index and approach for clinicians, enabling more precise cardiac electrophysiological signal analysis and interpretation. For P-wave analysis, the MC calculation is simplified to characterize only part of the cardiac signals, such as 100 ms. window from P-wave initiation to R-wave synchronization. In the middle or high frequency analysis of cardiac signals, for both surface ECG and intra-cardiac electrograms, the mutual correspondence calculation window is adjusted to cover only the QRS complex signal, which is a higher frequency signal than the P-wave or T-wave. The adjustable windowed mutual correspondence calculation provides more stable and sensitive results for specific applications, such as a particular arrhythmia (AF or Atrial Flutter), or cardiac depolarization (QRS) monitoring.

Mutual correspondence calculation analysis and diagnosis is very useful in identifying cardiac disorders, differentiating cardiac arrhythmias, characterizing pathological severities, prediction of life-threatening events. Its use can significantly improve heart medical treatment, including ongoing drug delivery during long term cardiac care, e.g., with Holster Monitoring.

The systems and processes described are not exclusive. Other systems and processes are derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIG. 2. Further, any of the functions and steps provided in FIGS. 1-6 may be implemented in hardware, software or a combination of both and may reside on one or more processing devices located at any location of a network linking the elements of FIG. 2 or another linked network, including the Internet.

What is claimed is:

1. A method of analyzing cardiac electrophysiological signals, the method comprising the activities of:

acquiring a set of signal data representing a plurality of cardiac electrophysiological signals as a function of time;

identifying individual signals within the set of acquired signal data, an individual signal comprising data values representing a plurality of sample points over a single heartbeat;

selecting one of the identified individual signals or a derived signal representing an average of a subset of the identified individual signals as an analysis signal having a plurality of first sample points of said plurality of sample points;

identifying data representing a reference signal, the reference signal comprising data values representing a plurality of second sample points;
aligning the first and second sample points;
calculating using a probability function, a single value representative of differences between the aligned corresponding first and second sample points; and
communicating data indicating the calculated single value to a destination for viewing by a user.

2. A method of analyzing cardiac electrophysiological signals, the method comprising the activities of:
acquiring a set of signal data representing a plurality of cardiac electrophysiological signals as a function of time;
identifying individual signals within the set of acquired signal data, an individual signal comprising data values representing a plurality of sample points over a single heartbeat;
selecting one of the identified individual signals or a derived signal representing an average of a subset of the identified individual signals as an analysis signal having a plurality of first sample points of said plurality of sample points;
identifying data representing a reference signal, the reference signal comprising data values representing a plurality of second sample points;
aligning the first and second sample points;
calculating a single value representative of differences between the aligned corresponding first and second sample points; and
communicating data indicating the calculated single value to a destination for viewing by a user wherein
the reference and analysis signals represent cardiac electrical activity and the activity of calculating the single value is a calculation of mutual correspondence, performed according to:

$$MC(S_1, S_2) = \sum_{i=1}^{N} p_i(s_{1i}, s_{2i})/N$$

wherein $S_1$ is the reference signal represented over a set of sample points i numbered from 1 to N, $S_2$ is an analysis signal represented over a set of sample points i numbered from 1 to N, and $p_i(s_{1i},s_{2i})$ is a joint probability function for data values between the corresponding sample points of $S_1$ and $S_2$.

3. The method of claim 1, wherein the activity of calculating the single value is a calculation of mutual correspondence, performed according to:

$$MC(S_1, S_2) = \left[\sum_{i=1}^{N} \min\_\text{amplitude}(s_{1i}, s_{2i}) \max\_\text{amplitude}(s_{1i}, s_{2i})\right]/N$$

wherein $S_1$ is the reference signal represented over a set of sample points i numbered from 1 to N, $S_2$ is analysis signal represented over a set of sample points i numbered from 1 to N, $\min(s_{1i},s_{2i})$ is the lesser of the data values of $s_{1i}$ and $s_{2i}$ for each corresponding sample point i, and $\max(s_{1i},s_{2i})$ is the greater of the data values of $s_{1i}$ and $s_{2i}$; for each corresponding sample point i.

4. The method of claim 1, wherein the activity of calculating the single value further includes the activities of:
transforming the signal data of the reference signal from data as a function of time to data as a function of frequency;
transforming the signal data of the analysis signal from data as a function of time to data as a function of frequency;
calculating a mutual correspondence between the reference signal and the analysis signal using the data as a function of frequency; and
calculating a time-frequency mutual correspondence value between the reference signal and the analysis signal, performed according to:

$$MC_{time-frequency} = 1 - \frac{\|A - B\|}{\|A + B\|}$$

wherein A is the value representative of mutual correspondence of the reference signal and the analysis signal calculated using data as a function of time, B is the value representative of mutual correspondence of the reference signal and the analysis signal signal calculated using data as a function of frequency, and $\|x\|$ represents the absolute value operator.

5. The method of claim 1, wherein the activity of calculating the single value further includes the activities of:
transforming the signal data of the reference signal from data as a function of time to signal data as a function of other variables;
transforming the signal data of the analysis signals from data as a function of time to signal data as a function of other variables;
calculating a mutual correspondence between the reference signal and the analysis signal for each set of transformed signal data; and
calculating a value representative of a multi-dimensional mutual correspondence of the reference signal and the analysis signal, performed according to:

$$MC_{multi-dimension} = 1 - \frac{\sum_N \|A_i - \overline{A}\|}{\sum_N \|A_i\|}$$

where $A_i$ is the value representative of a mutual correspondence of the reference signal and the analysis signal as a function of each variable to which the reference signal and the analysis signal were transformed; $\overline{A}$ is the average value of the value representative of a mutual correspondence of the reference signal and the analysis signal as a function of each variable to which the reference signal and the analysis signal were transformed; and N is the number of different variables to which the signal data was transformed.

6. The method of claim 5, wherein the set of signal data acquired represents electrocardiogram signals for a patient and a value representative of the mutual correspondence of the reference signal and the analysis signal is provided to assist in the monitoring or diagnosis of cardiac electrophysiological changes.

7. The method of claim 5, wherein the activity of calculating a value representative of the mutual correspondence of the reference signal and the analysis signal is performed only over a selected portion of an electrocardiogram signal.

8. The method of claim 1, wherein the reference signal is one of: (a) derived by an averaging calculation of one of, a set of signals from a patient and cardiac electrophysiological signal data from a repository.

9. The method of claim 1, wherein the reference signal is derived from one of: (a) current electrocardiogram signals for a patient, (b) previous electrocardiogram signals for the patient, and (c) previous electrocardiogram signals for patients whose physical characteristics match the patient.

10. A system for analyzing cardiac electrophysiological signals, the system comprising:
- an acquisition processor for acquiring a set of signals representing a plurality of cardiac electrophysiological signals as a function of time;
- a signal processor coupled to said acquisition processor for
  - identifying individual signals within the set of acquired signals, each individual signal comprising data values on a plurality of sample points over a single heartbeat;
  - selecting one of the identified individual signals or an average of a subset of said identified individual signals to obtain an analysis signal having a plurality of first sample points of said plurality of sample points,
  - identifying data representing a reference signal, the reference signal comprising data values representing a plurality of second sample points, and
  - aligning the first and second sample points;
- a calculation processor coupled to said signal processor for calculating using a probability function, a value representative of differences between the aligned corresponding first and second sample points; and
- an output processor coupled to said calculation processor for outputting the calculated value to a user.

11. The system of claim 10, wherein said set of signals acquired by said acquisition processor comprises electrocardiogram signals.

12. The system of claim 11, wherein said signal processor averages a plurality of electrocardiogram signals to remove noise and artifacts from the acquired set of signals.

13. The system of claim 10, wherein said calculation processor operates to calculate said value representative of differences between the reference signal and the analysis signal by calculating mutual correspondence, according to:

$$MC(S_1, S_2) = \sum_{i=1}^{N} p_i(s_{1i}, s_{2i})/N$$

wherein $S_1$ is the reference signal represented over a set of sample points i numbered from 1 to N, $S_2$ is an analysis signal represented over a set of sample points i numbered from 1 to N, and $p_i(s_{1i}, s_{2i})$ is a joint probability function for data values between the corresponding sample points of $S_1$ and $S_2$.

14. The system of claim 10, wherein said calculation processor operates to calculate said value representative of differences between aligned corresponding first and second sample points, according to:

$$MC(S_1, S_2) = \left[\sum_{i=1}^{N} \text{min\_amplitude}(s_{1i}, s_{2i}) \text{max\_amplitude}(s_{1i}, s_{2i})\right]/N$$

wherein $S_1$ is the reference signal represented over a set of sample points i numbered from 1 to N, $S_2$ is analysis signal represented over a set of sample points i numbered from 1 to N, $\min(s_{1i},s_{2i})$ is the lesser of the values of $s_{1i}$ and $s_{2i}$ for each corresponding sample point i, and $\max(s_{1i},s_{2i})$ is the greater of the values of $s_{1i}$ and $s_{2i}$ for each corresponding sample point i.

15. The system of claim 10, further comprising
- a memory coupled to said acquisition processor and said signal processor for storing the acquired set of signals and, wherein
- said signal processor transforms a stored set of signal data as a function of time into a set of signal data as a function of frequency and stores the set of transformed signal data in said memory.

16. The system of claim 14, wherein said calculation processor
- calculates mutual correspondence between the reference signal and the analysis signal as a function of frequency; and
- calculates a time-frequency mutual correspondence between the reference signal and the analysis signal, performed according to:

$$MC_{time\text{-}frequency} = 1 - \frac{\|A - B\|}{\|A + B\|}$$

wherein A is the mutual correspondence between the reference signal and the analysis signal calculated as a function of time, B is the mutual correspondence between the reference signal and the analysis signal calculated as a function of frequency, and $\|x\|$ represents an absolute value operator.

17. The system of claim 10, further comprising
- a memory coupled to said acquisition processor and said signal processor for
- storing the acquired set of signals and, wherein
- said signal processor transforms a stored set of signal data as a function of time into sets of signal data and transforms the signal data of the analysis signals as a function of time into sets of signal data; and
- said calculation processor calculates the mutual correspondence $A_i$ between the reference signal and the analysis signal for each set of signal data and transformed signal data, to produce a value representing a multi-dimensional mutual correspondence between the reference signal and the analysis signal, according to:

$$MC_{multi\text{-}dimension} = 1 - \frac{\sum_{N} \|A_i - \overline{A}\|}{\sum_{N} \|A_i\|}$$

where $A_i$ comprises a mutual correspondence for each domain; $\overline{A}$ is the average value of the mutual synchronicities of all domains; and N is the number of different domains to which signal data is transformed.

* * * * *